United States Patent
Belli

(10) Patent No.: US 7,144,379 B2
(45) Date of Patent: Dec. 5, 2006

(54) AUTOMATIC APPARATUS FOR CONTROLLING THE CHILDBIRTH LABOR

(76) Inventor: Pierfrancesco Belli, Via San Gallo 78, I-50129 Florence (IT)

( * ) Notice: Subject to any disclaimer, the term of this patent is extended or adjusted under 35 U.S.C. 154(b) by 0 days.

(21) Appl. No.: 10/537,005
(22) PCT Filed: Nov. 3, 2004
(86) PCT No.: PCT/IT2004/000602

§ 371 (c)(1),
(2), (4) Date: May 26, 2005

(87) PCT Pub. No.: WO2005/051185

PCT Pub. Date: Jun. 9, 2005

(65) Prior Publication Data

US 2005/0283056 A1  Dec. 22, 2005

(30) Foreign Application Priority Data

Nov. 25, 2003  (IT)  .............................. FI2003A0298

(51) Int. Cl.
  *A61B 5/103*  (2006.01)
  *A61B 17/42*  (2006.01)
  *A61B 5/00*   (2006.01)
(52) U.S. Cl. ...................... 600/588; 600/304; 600/546; 600/587; 606/119
(58) Field of Classification Search ................ 600/300, 600/301, 304, 546, 587, 588, 591, 595; 606/119, 606/121, 122, 124, 202, 200; 601/45, 151, 601/152
  See application file for complete search history.

(56) References Cited

U.S. PATENT DOCUMENTS

| | | | |
|---|---|---|---|
| 4,989,615 A * | 2/1991 | Hochberg ...................... 3/587 |
| 5,174,281 A * | 12/1992 | Lee .............................. 601/45 |
| 5,289,827 A * | 3/1994 | Orkin et al. ................. 600/588 |
| 5,373,852 A | 12/1994 | Harrison et al. |
| 5,405,356 A | 4/1995 | Hahn et al. |
| 5,645,563 A * | 7/1997 | Hahn et al. .................. 606/202 |
| 5,871,499 A * | 2/1999 | Hahn et al. .................. 606/202 |
| 2002/0193701 A1 | 12/2002 | Simpson et al. |
| 2005/0010127 A1* | 1/2005 | Calderon et al. ........... 600/546 |

FOREIGN PATENT DOCUMENTS

WO    WO 99/19704    4/1999

* cited by examiner

*Primary Examiner*—Charles A Marmor, II
(74) *Attorney, Agent, or Firm*—McGlew & Tuttle, PC

(57) ABSTRACT

Apparatus for controlling the childbirth labor comprising an electromyographic unit (4) with sensors (3) for detecting electrical signals of a parturient's uterus and means (6) for analyzing and processing the electrical signals, and a pneumatic belt (1) to be fixed around the parturient's abdomen having sensors (15) to detect the variation of the internal pressure due to uterine contractions, and means (2) for inflating the belt to provide a thrust as an aid for the expulsion of the fetus, where a device (7) is provided, associated with sensors (15) and (3) to control the activation of means (2) for the inflation of the pneumatic belt (1).

18 Claims, 3 Drawing Sheets

AUTOMATIC APPARATUS FOR CONTROLLING THE CHILDBIRTH LABOR

FIELD OF THE INVENTION

The present invention refers to an automatic apparatus for controlling the childbirth labor.

BACKGROUND OF THE INVENTION

It is known that the term "childbirth labor" refers to the complex of mechanical and dynamic phenomena which lead to the expulsion of the fetus and placenta and which, conventionally, is subdivided into three stages. The first stage, which relates to the dilatant period, that is, to the beginning of the labor up to the complete dilatation of the uterine cervix, is in turn subdivided into a "latent period", characterized by a dilatation of 3–4 cm, and a following "active period" which leads to a complete 15 dilatation. The second stage, which relates to the expulsive period, goes from the complete dilatation to the delivery. The third stage, which relates to the discharge of the after-birth, ends up with the expulsion of the placenta.

It is also known that the deficiency, alteration or insufficient coordination of the uterine contractions may cause problems upon the expulsive stage, which is the delivery's most delicate one. In particular, it may happen that the uterus is not able to produce, with its contractions, a force of an intensity sufficient to conclude the delivery's expulsive stage (hypokinesia). It may happen, besides, that the expectant mother, in spite of the therapies commonly provided for treating such cases, is unable to produce a thrust—through a corresponding contraction of the abdominal press—adding up to the force generated by the uterine contraction. And, since a prolonged rest of the fetus in the delivery duct may seriously endanger the health condition thereof, a so-called Kristeller maneuver is generally performed by the health personnel, which consists in exerting, with an arm, a series of thrusts upon the bottom of the uterus, with the purpose of assisting the natural expulsive forces and speeding up the progression and disengagement of the fetus. However, this maneuver has risks inasmuch as it may cause the rupture of the uterus, the detachment of the placenta and acute fetal pains as well.

Also known in obstetrics is the use of the electromyograph (EMG) by which it is possible to register the electrical phenomena of the uterus' natural and involuntary contractions by deriving the relevant electrical potentials via electrodes applied on the patient's abdomen: an application software to be run on a PC provides for a graph of said electrical potentials versus time. However, the use of only an EMG does not provide any aid to the parturient's thrust and, moreover, the contraction graphs plot also other spurious signals such as spikes, tensions induced by the activation of other apparatuses and by neon glow lamps.

Also known in obstetrics is the use of the Pressure Labor Assister (PLA), with pressure sensors-controlled software, which utilizes the pressure increase inside an air chamber—formed within an abdominal band fixed around the patient's body—and which occurs as a consequence of the natural uterine contractions, to provide an automatic extra force, as an aid to the parturient, for the expulsion of the future baby.

On the other hand, this known device PLA does not provide a chart nor a record of the uterine contractions, and may also be a source of dangers, inasmuch as the possible overpressures on the pneumatic band, which are independent of the contractions but are due instead, for example, to more or less involuntary movements of the parturient, are always interpreted as a signal of uterine contraction and, in such case, it may occur that the consequent inflation of the abdominal pneumatic band will take place during a rest period, between one contraction and another, thereby dangerously reducing the inflow of blood to both the parturient and future baby.

SUMMARY OF THE INVENTION

One object of the present invention is to overcome the drawbacks of the common and widespread Kristeller technique.

A further object of the present invention is to enable, in case of ascertained insufficient expulsive force of the uterine natural contractions, the person in charge of the childbirth to activate a device providing an extra thrust for the expulsion of the fetus—the activation of said device depending, for a higher safety measure, on the uterine contraction and not on false signals.

The advantages deriving from the present invention lie essentially in the fact that it is possible to automatically ensure, whenever the need arises and in a non-invasive fashion, the highest accurate coordination between the internal thrust produced by both natural and involuntary uterine contractions and the supplementary thrust produced by means of a pneumatic belt intended to act on the parturient's abdomen; that an apparatus according to the invention is safe, utilizable with relative simplicity by the personnel assisting the expectant mothers, relatively simple to make and reliable also after a prolonged service period. All this by making use of an integrated system allowing the auxiliary pneumatic thrust to be obtained only when the parturient has contractions detected simultaneously and safely by both pneumatic and electrical signals independent from each other and deriving from said contractions.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
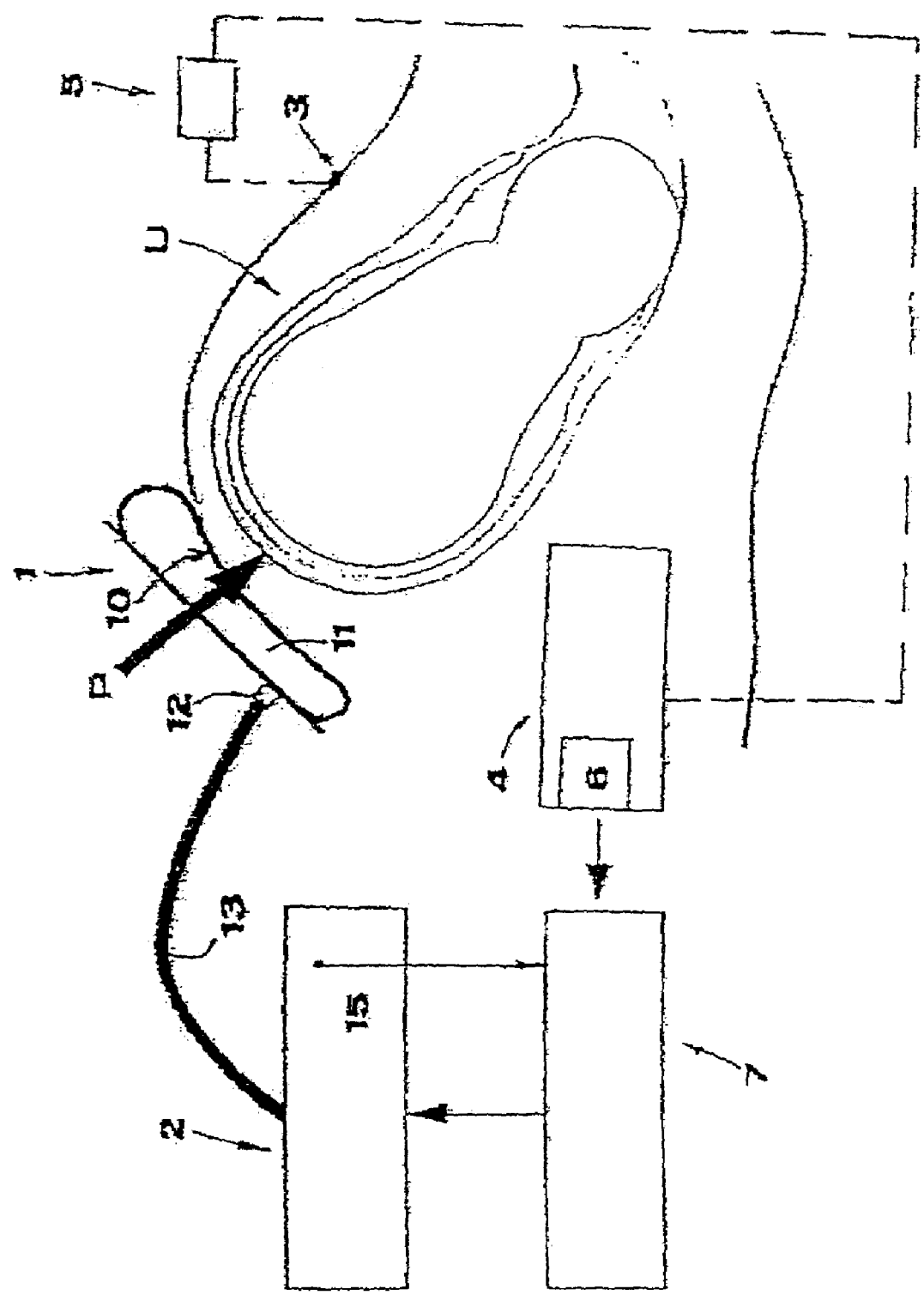
FIG. 1 is a simplified block diagram of an apparatus according to the invention, showing a possible configuration thereof upon use.
Figure 2:
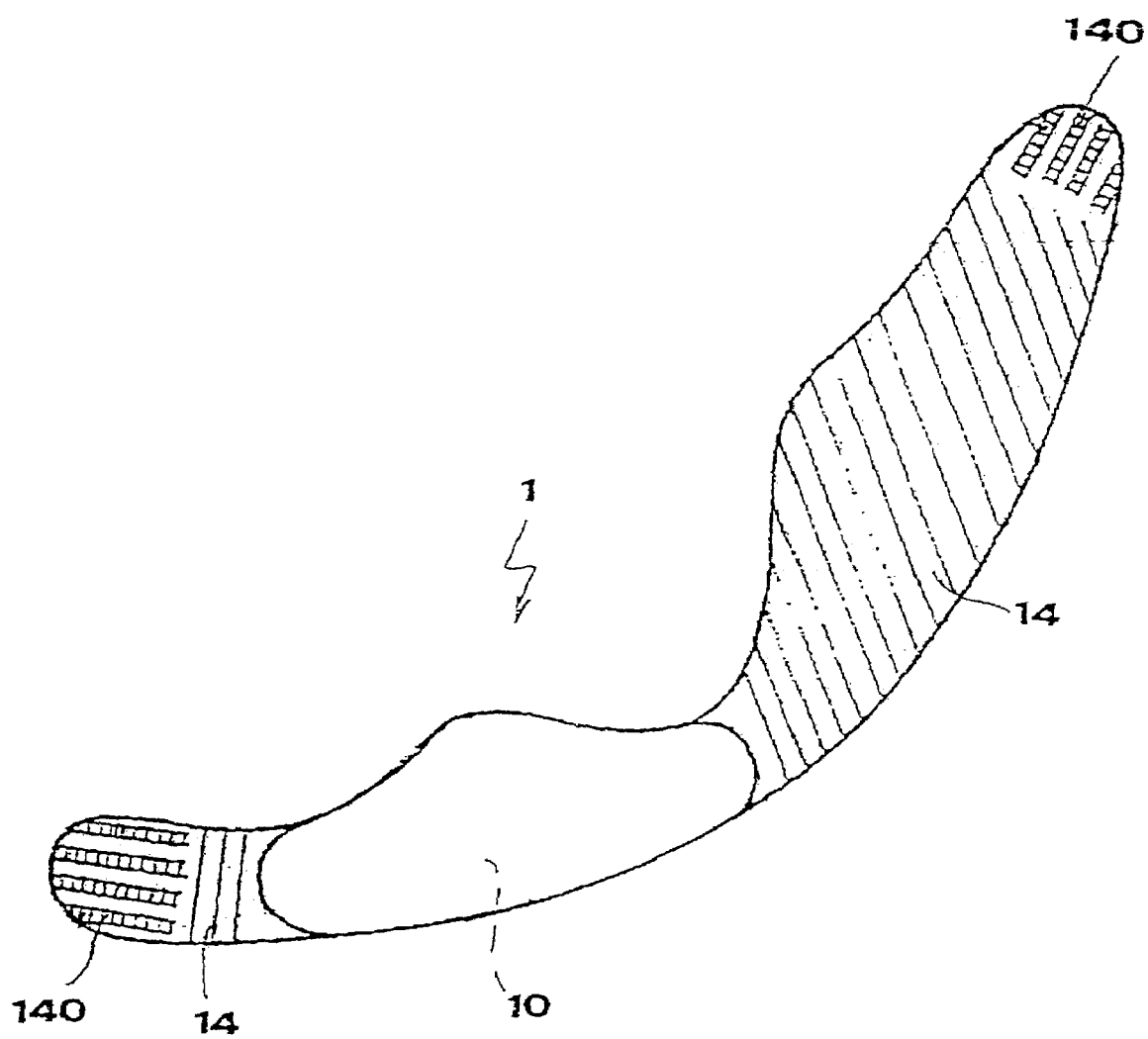
FIG. 2 is a schematic plan view of the pneumatic belt (1) shown in the schematic diagram of FIG. 1.

Referring to the drawings in particular, FIG. 1 shows a means for detecting the electrical activity of the uterus, comprising two or more outer electromyographic sensors (3) (that is, sensors of non-invasive type) able to be positioned on the skin of the parturient's abdomen at two regions corresponding to preset points of the uterus U. Also provided are a means for registering and plotting the electrical signals of the uterine contractions thus detected and a means, which includes an electromyographic apparatus (4) and an interface (5), for analyzing electrical signals in relation to a predetermined scheme of analysis. An inflatable belt (1) is provided that is associated with pneumatic means (2) able to inflate it under control and at preset pressure, and respectively deflate it. The belt (1) is put on by the expectant mother in such a way that a surface (10) of the same belt will act, when inflated, upon the bottom of the uterus. A means (7) is provided to control the activation and deactivation of said pneumatic means (2) in response to the pressure variation due to the contraction and sensed by the pneumatic belt, and to the result of analysis of the uterus' electrical activity.

In particular, the analysis means comprise an electromyographic apparatus (4), associated with said sensors (3) via an interface (5) allowing the amplification and preprocessing of the signals and provided with a section (6) for processing the signals detected by the sensors (3) and transmitted through the interface (5) with their respective time value, as best described later on in greater detail.

In case of two-channel electromyographic apparatuses, such as the TECA Sinergy Multimedia of the Oxford Instruments, two channel sensors or electrodes and one ground electrode are used: the channel sensors are positioned symmetrically and horizontally in a skin region of the parturient's abdomen at about 5–15 cm of the umbilical transverse, and the ground electrode is located on the internal side of the left thigh. As for the inflatable belt (1), this is of a type comprising an air chamber (11) with a coupling (12) for a tube (13) connectable to said means (2), and provided with two wings (1a) of a length sufficient for being tied up around the parturient's thorax: the wings (14) being able to be linked one to the other by Velcro-type means 140 after the belt has put on. Moreover, the pneumatic means (2) is internally provided with sensors (15) able to detect the pressure variations inside the air chamber (11), which are due to the thrusts exerted by the parturient's abdomen as a consequence of the uterine contractions, that is, relative to a basic pressure value corresponding to the initial inflation (for example, when using a belt of MITECH-200-A type, a basic value of 8–16 kPa). The belt in question is intended to exert, as best described later on, a predetermined pressure P uniformly distributed on the uterus' bottom.

Provided upstream of said pneumatic means (2) is an activation device (7) which, in turn, is associated with sensors (15) located within the means (2), and with the electromyographic apparatus (4): the device (7) determining the activation of the pneumatic means (2), that is, the inflation of the belt (1), whenever both the uterine contraction signals on output from the sensors (15) and the signals on output from the apparatus (4) are present therein at the same time.

To be more precise, if, during the labor, the device (7) receives simultaneously both the electrical signals from the means (4)—resulting of such intensity and shape as to correspond to those of the uterine contractions (for example, electrical signals three times higher than the signals sensed between one contraction and another)—and the pneumatic signals detected by the sensors (15) and identified as contraction signals as well, then, only in this case the device (7) gives the command for the activation of the means (2), that is, for the inflation of the belt (1) at a pressure to be either preset or timely established by the person in charge of the childbirth.

In other words, the activation of belt (1) and, accordingly, the auxiliary thrust P exerted by the latter on the parturient's abdomen in correspondence of the uterus' bottom, takes place solely when there is occurring, simultaneously, on the one hand, an overpressure in he chamber (11) of belt (1) due to a deformation imposed by the abdominal muscles on the belt's wall because of a contraction and, on the other hand, that is, in correspondence of sensors (3), a myoelectrical activity of preset intensity and in any case exceeding the intensity being present when no contractions occur. The two detections are independent from each other, as being obtained from independent detection means, but are both related to a same event, that is, to the natural and involuntary uterine contraction upon the active stage of the childbirth. It thus follows that the actuation of the belt (1) results precisely in phase with the uterine contractions of greater intensity, as it is operated on the basis of detections made both within the chamber (11) of belt (1) and on the basis of detections made on the muscular electrical activity in the more directly involved abdominal region.

The time for the activation of belt (I), that is, the time of overpressure persistence within the chamber (11) of the same belt under control of means (2), is adjustable by the health operator who assists the expectant mother and whose decisions are taken according to the trend of the electromyographic contraction signals previously registered for the same patient.

As above described, the device (7) which controls the activation of the means (2) provided for the inflation of the belt (1) is commonly associated with the pressure sensors (15) and with the electrical sensors (3) as well. However, the operator may cut off one or the other connection, owing to a malfunction of one of them or when he/she deems suited to do so. For example, it is possible to exclude the connection with the pressure sensors (15) so that the activation of the pneumatic means (2) is controlled solely by electrical signals transmitted by the sensors (3); otherwise, it is possible to cut off the sensors (3), so that the activation of the pneumatic means (2) is controlled solely by pressure signals transmitted by the sensors (15). All this makes it possible to use the device in question also in case of malfunctions affecting either the detection of pressure signals through the sensors (15) or the detection of signals transmitted by the sensors (3), and to process the signals by 10 means of the electromyographic apparatus (4, 6). In any case, the operator has faculty of excluding the automatic intervention of the system in order to use the latter only when the need arises.

Figure 3:
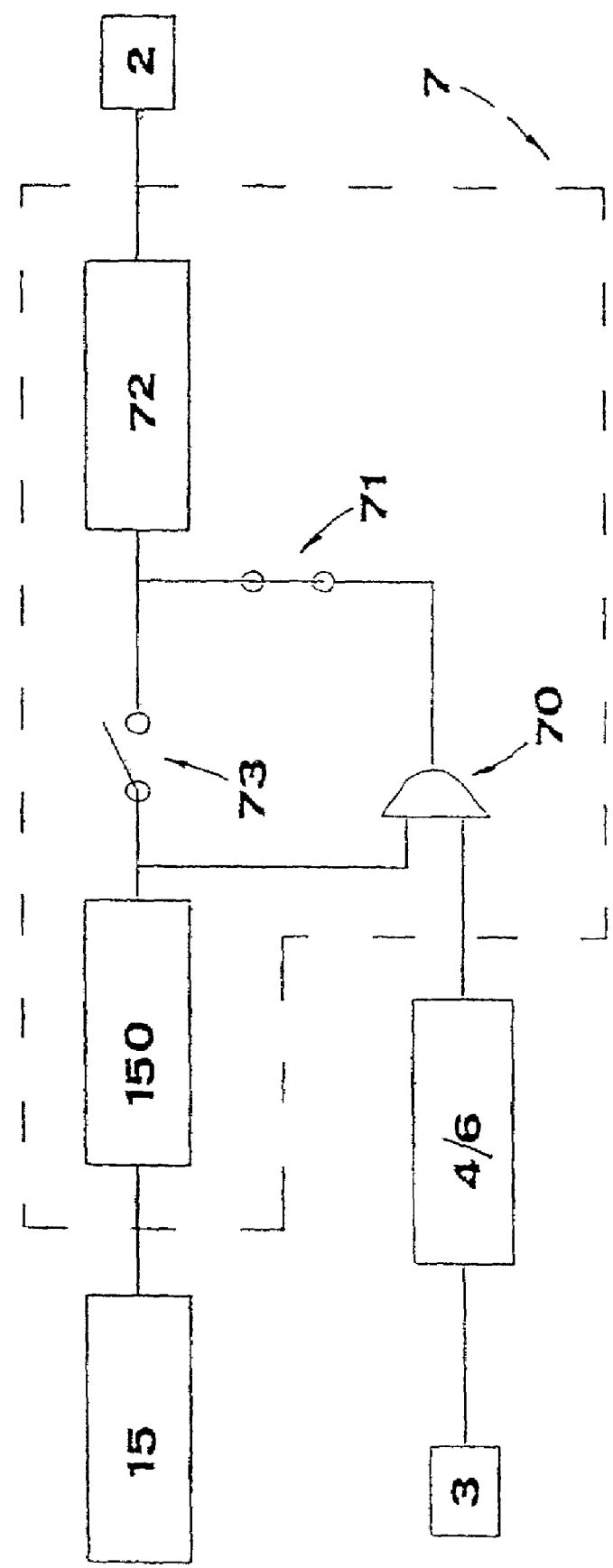
FIG. 3 is a further simplified block diagram of an apparatus according to the invention.

With reference to the diagram of FIG. 3, the device (7) comprises an AND gate (70) whose inputs are connected, respectively, to the output of the apparatus (4) and to the output of an A/D converter (150) provided downstream of sensors (15) housed in the belt (1). The output of said AND gate is connected with the input of a D/A converter (72) which, on output, is connected with the means (2) which activate the inflation of the belt (1). Inserted on the line connecting the gate (70) with the converter (72) is a normally closed switch (71). Inserted on the line connecting the converter (150) with the converter (72) is a normally opened switch (73). When the sensors (15) sense an overpressure in the chamber of belt (1), a corresponding electrical signal is produced which, after being converted in digital form by the converter (150), is fed to the AND gate (70). Similarly, the signals on output from the section (6) of the electromyographic apparatus (4) come to the AND gate (70) which, when both signals are present, activates, through the converter (72), the opening of a solenoid of means (2) and, therefore, the inflation of the belt (1). The operator may decide to cut off the AND gate (70), for example in case of ascertained failure of the apparatus (4), by merely opening the switch (71) and closing the switch (73). The switches (71) and (73) operate in push-pull mode.

The data processing section (6) can advantageously consist of a PC associated with the electromyographic unit (4). Within the section (6), the signals coming from the sensors (3) and acquired by the system are processed according to a preset algorithm, for example, the one described in the article "A fast algorithm for detecting contractions in uterine electromyography—a non invasive method utilizing higher-order zero crossing for signal analysis" published in IEE Engineering and Biology—March/April 2000. Such an algorithm allows the obtainment of an estimator value to be compared with a predefined threshold. Throughout the time interval in which the estimator value exceeds said threshold, it is assumed that a contraction is taking place and a signal of logic level one is fed to the AND gate (70). Vice versa, when the estimator value is below said threshold value, a signal of logic level zero is fed to the AND gate (70).

While specific embodiments of the invention have been shown and described in detail to illustrate the application of the principles of the invention, it will be understood that the invention may be embodied otherwise without departing from such principles.

The invention claimed is:

1. Apparatus for controlling childbirth labor comprising:
   an electromyographic unit with sensors associated therewith for detecting the electrical signals of a parturient's uterus and means for analyzing and processing said electrical signals;
   a pneumatic belt to be fixed around the parturient's abdomen and having sensors associated therewith to detect the variations of internal pressure of an interior of said pneumatic belt due to uterine contractions, and means for inflating said belt to provide a thrust as an aid for the expulsion of the fetus; and
   a device associated with the electromyographic unit and the pneumatic belt sensors and to control the activation of said means for inflating the pneumatic belt.

2. Apparatus according to claim 1, characterized in that said device comprises an AND gate with AND gate inputs being connected, respectively, to an output of said electromyographic unit and to an output of an A/D converter located downstream of said sensors which are associated with the belt, and with an AND gate output being connected with the input of a D/A converter, wherein the D/A converter output is connected with said means for inflating the belt.

3. Apparatus according to claim 2, characterized in that a first switch is inserted on a line connecting the AND gate with the D/A converter.

4. Apparatus according to claim 3, characterized in that a second switch is inserted on a line connecting the A/D converter with the D/A converter, said second switch operating in push-pull mode with respect to said first switch.

5. Apparatus according to claim 2, characterized in that a second switch is inserted on a line connecting the A/D converter with the D/A converter.

6. Apparatus according to claim 1, characterized in that said means for analyzing and processing of the electromyographic unit consist of a PC associated with the electromyographic unit.

7. Apparatus for controlling childbirth labor, said apparatus comprising:
   an electromyographic unit with sensors associated therewith for detecting electrical signals of a parturient's uterus;
   means for analyzing and processing said electrical signals; and
   a pneumatic belt adapted to be fixed around a parturient's abdomen having sensors associated therewith to detect the variations of an internal pressure of an interior of said pneumatic belt due to uterine contractions; and
   means for inflating said belt to provide a thrusting force to aid in expulsion of a fetus, including a control associated with the electromyographic unit and the pneumatic belt sensors for controlling the activation of said means for inflating said pneumatic belt.

8. Apparatus according to claim 7, wherein said device comprises an AND gate with AND gate inputs being connected, respectively, to an output of said electromyographic unit and to an output of an A/D converter located downstream of said sensors which are associated with the belt, and with an AND gate output being connected with the input of a D/A converter, wherein the D/A converter output is connected with said means for inflating the belt.

9. Apparatus according to claim 8, wherein a first switch is inserted on a line connecting said AND gate with said D/A converter.

10. Apparatus according to claim 9, wherein a second switch is inserted on a line connecting the A/D converter with the D/A converter, said second switch operating in push-pull mode with respect to said first switch.

11. Apparatus according to claim 8, wherein a second switch is inserted on a line connecting the A/D converter with the D/A converter.

12. Apparatus according to claim 7, wherein said means for analyzing and processing of the electromyographic unit comprises a PC associated with the electromyographic unit.

13. Apparatus for controlling childbirth labor, said apparatus comprising:
   a pneumatic belt to be fixed around a parturient's abdomen;
   a means for inflating said pneumatic belt providing a thrust as an aid for explusion of a fetus;
   electromyographic sensors;
   pressure sensors;
   a device for controlling activation of inflation means of said pneumatic belt, wherein said device is responsive to signals from electromyographic sensors and to pressure sensors that detect variations of internal pressure within said pneumatic belt due to uterine contractions; and
   a means for analyzing and processing said signals.

14. Apparatus according to claim 13, wherein said device comprises an AND gate with AND gate inputs being connected, respectively, to an output of said electromyographic sensors and to an output of an A/D converter located downstream of said pressure sensors for detecting variations of internal pressure within the belt, and with an AND gate output being connected with the input of a D/A converter, wherein the D/A converter output is connected with said means for inflating the belt.

15. Apparatus according to claim 14, wherein a first switch is inserted on a line connecting said AND gate with said D/A converter.

16. Apparatus according to claim 15, wherein a second switch is inserted on a line connecting the A/D converter with the D/A converter, said second switch operating in push-pull mode with respect to said first switch.

17. Apparatus according to claim 14, wherein a second switch is inserted on a line connecting the A/D converter with the D/A converter.

18. Apparatus according to claim 13, wherein said means for analyzing and processing said signals comprises a PC associated with the electromyographic sensors.

* * * * *